United States Patent
Lipo

(10) Patent No.: US 7,207,935 B1
(45) Date of Patent: Apr. 24, 2007

(54) METHOD FOR PLAYING MUSIC IN REAL-TIME SYNCHRONY WITH THE HEARTBEAT AND A DEVICE FOR THE USE THEREOF

(76) Inventor: Mordechai Lipo, 117 Harav Uxiel St., 96431 Jerusalem (IL)

( * ) Notice: Subject to any disclaimer, the term of this patent is extended or adjusted under 35 U.S.C. 154(b) by 518 days.

(21) Appl. No.: 10/130,476

(22) PCT Filed: Nov. 19, 2000

(86) PCT No.: PCT/IL00/00770

§ 371 (c)(1),
(2), (4) Date: Sep. 4, 2002

(87) PCT Pub. No.: WO01/37914

PCT Pub. Date: May 31, 2001

(30) Foreign Application Priority Data

Nov. 21, 1999 (IL) .................................. 133061

(51) Int. Cl.
*A61M 21/00* (2006.01)
(52) U.S. Cl. ............................................... 600/28
(58) Field of Classification Search ................ 128/897, 128/898; 600/26–28, 500–503
See application file for complete search history.

(56) References Cited

U.S. PATENT DOCUMENTS

| | | | | |
|---|---|---|---|---|
| 4,181,134 A | * | 1/1980 | Mason et al. | ............... 600/502 |
| 4,282,864 A | * | 8/1981 | Pizer | ............... 600/26 |
| 4,436,096 A | * | 3/1984 | Dyck et al. | ............... 600/502 |
| 4,896,675 A | | 1/1990 | Ohsuga et al. | |
| 6,230,047 B1 | * | 5/2001 | McHugh | ............... 600/519 |
| 6,370,433 B1 | * | 4/2002 | Hartlaub et al. | ............... 607/32 |
| 6,554,763 B1 | * | 4/2003 | Amano et al. | ............... 600/26 |
| 6,634,992 B1 | * | 10/2003 | Ogawa | ............... 482/8 |

FOREIGN PATENT DOCUMENTS

| | | |
|---|---|---|
| DE | 354052 | 6/1987 |
| DE | 9418874 | 10/1995 |
| WO | WO 9517854 | 7/1995 |

OTHER PUBLICATIONS

McKinney et al., "Effects of Guided Imagery and Music (GIM) Therapy on Mood and Cortisol in Healthy Adults." *Health Psychology*. vol. 16, Issue 4: pp. 390-400. Jul. 1997.
Goldberger, Ary L. "Fractal Mechanisms in the Electrophysiology of the Heart". *IEEE Engineering in Medicine and Biology*. Jun. 1992. 11 (2): 47-52.

* cited by examiner

*Primary Examiner*—Samuel G. Gilbert
(74) *Attorney, Agent, or Firm*—Browdy and Neimark, PLLC

(57) ABSTRACT

A method and device for presenting music to a patient in real time synchrony with relation to every single pulse of the patient's heartbeat, thereby inducing an enjoyable and relaxing sensation. A digitized electric signal representative of the patient's heartbeat is fed to a microprocessor which brings the digitized electric signal into correspondence with a sequence of musical sound configurations so that each pulse beat is followed by one of the sound configurations in real time. The sequence of musical sound configurations is presented to the patient so that each sound configuration is played in real-time synchrony with a respective pulse beat.

33 Claims, 1 Drawing Sheet

Figure 1:
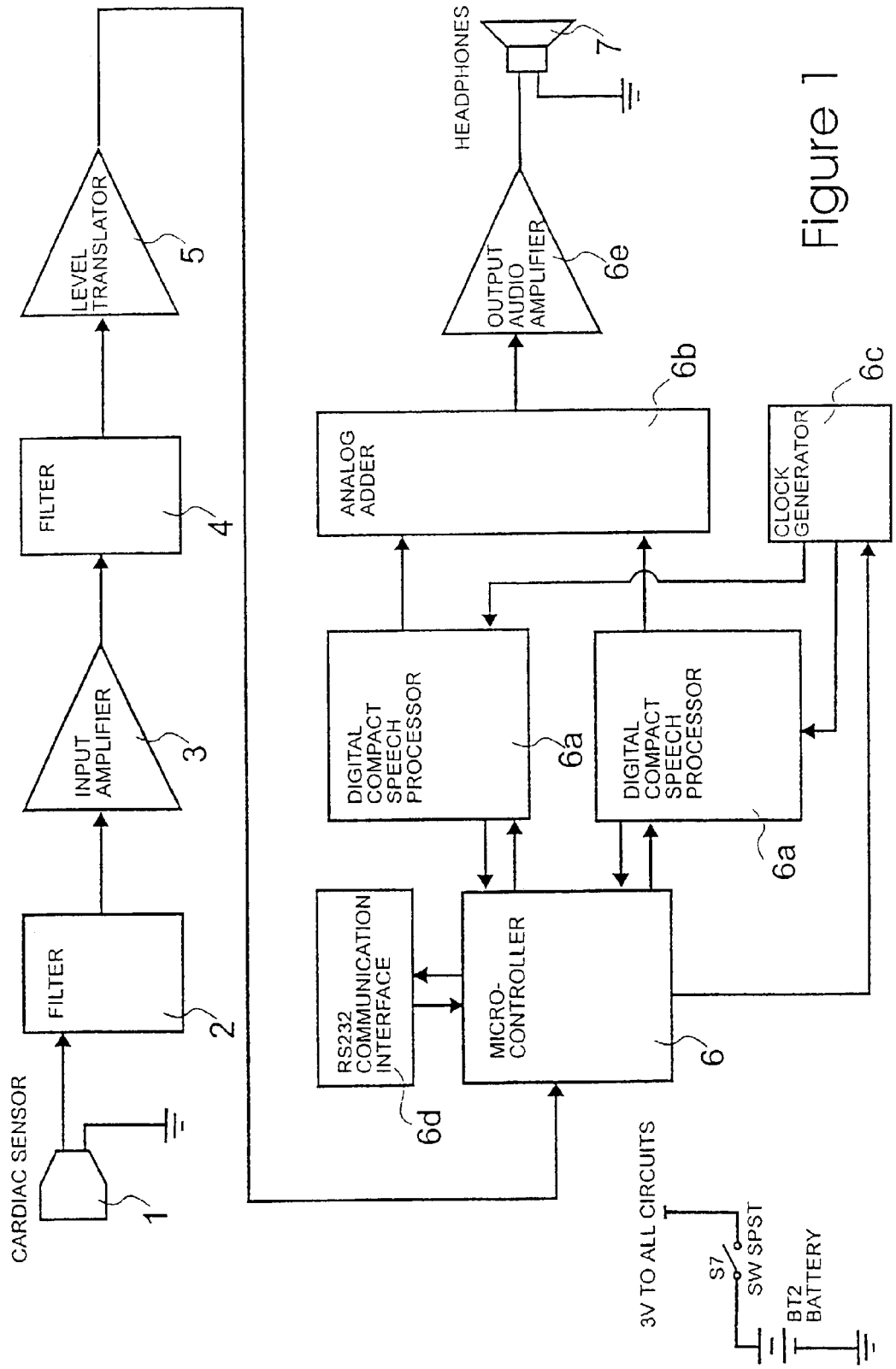

METHOD FOR PLAYING MUSIC IN REAL-TIME SYNCHRONY WITH THE HEARTBEAT AND A DEVICE FOR THE USE THEREOF

FIELD OF THE INVENTION

The present invention relates to the field of music therapy.

BACKGROUND OF THE INVENTION

The positive influence of music corresponding with a patient's heartbeat on the patient's mental and physical health is known in music therapy. The improvement of mood, decrease of depression and level of cortisone in blood after a number of treatment sessions with the use of such music was proved by special research conducted by the Department of Music Education and Music Therapy, the University of Miami, USA. (McKinney C H, Antony M H, Kumar M., Tims F C, McCabe P M, Health Psycho 1997 July; 16(4), P.390–400). According to the method used in said research, the music is played not in a real time synchrony with the patient's heartbeat.

The rhythm of a healthy individual's heartbeat is not constant. There are certain fluctuations in heartbeat rate from one pulse to another. Dr. Goldberger at Beth Israel Hospital offers a way of creation the music corresponding with heartbeat of a concrete patient (Eng. Med. Biol. Mag. 1992 June: 11(2), 47–52). In the course of his research, the patient pulse was measured over an entire day by a special monitor with a pocket-size electrocardiogram recorder, the precise intervals between the pulse beats were processed by means of a computer program in accordance with the requirements of statistics to eliminate short-term fluctuations caused by movement or breathing. The daily pulse beat sequence in which the fluctuations had come up was preserved. Thereafter, the time intervals between the heartbeats were converted into integers. Each integer, ranging from 1 to 18, was brought into correspondence with a note of diatonic musical scale. I.e., the changes in heart rate were made proportional to the changes in pitch of the sounds. Thus, a daily heartbeat melody of a patient was generated. Then, Dr. Goldberger chose the rhythm and harmonic accompaniment for each melody. The application of this music produced a positive effect on the state of mind of the patients. Dr. Goldberger explains the medicinal effect of these "heart songs" by the assumption that the variation in pitch of the sounds so produced resonates with the body's own complex variability and scaling.

A case in which physical stimuli corresponding with the patient's heartbeat are used is the invention by Pfizer Robert according to the U.S. Pat. No. 4,282,864. The invention relates to a device for inducing a pre-hypnotic state of profound relaxation in an individual, wherein the individual's mind is receptive to suggestion. The device is characterized in that biofeedback signals from the individual are used to produce a plurality of pulsed physical stimuli having a double frequency in relation to the heartbeat rate of the individual.

The device includes a heartbeat sensor for producing a first pulse signal, the pulse beats of which are in synchrony with the heartbeat of the individual. An interpolation device is connected with the heartbeat sensor to produce a second pulse signal, the pulses of which occur midway in time between successive pairs of heartbeat pulses, respectively. The interpolation device includes a voltage ramp generator responsive to the first pulse signal to produce a linear voltage ramp output the peaks of which are in synchronization with the pulses of the first signal, respectively, the amplitude of the voltage peaks corresponding with the heartbeat rate of the individual. The interpolation device further includes a peak detector for sensing the peaks of the voltage ramp output and a comparator connected with the peak detector for sensing the midpoint of the voltage ramp output between successive peaks to produce the second pulse signal. A physical stimulus device having a pair of inputs connected with the heartbeat sensor and the interpolation device, respectively, produces a pulsed physical stimulus in response to the first and second signals and having a frequency of twice the heartbeat rate of the individual. Application of such a biofeedback pulsed physical stimulus induces a pre-hypnotic state of profound relaxation in the individual.

Although the technology used in this device allows to present the stimuli to the patient in real time with the patient's heartbeat, the effect of double frequency of the stimuli expresses itself in above-mentioned pre-hypnotic state but not in the improvement of concentration, mood, and feeling of well being that we try to create in the patient with our method.

The method of the present invention allows playing music responsive to each pulse beat of the patient in real time. We assume that the effect of our invention is due to the simultaneous perception by the patient's brain of both the physiological effects produced by each real heartbeat and the music of the device which is in exact back response to the same heart beat.

SUMMARY OF THE INVENTION

The present invention relates to a method for the improvement of concentration, mood, reinforcement of the immune defense and slowing some of the aging processes in a patient by presentation to the patient of a sequence of musical sound configurations in real time synchrony with the patient's heartbeat with relation to every single pulse. The method according to the present invention comprises:

a) sensing and transmitting the patient's pulse into analog electric signal;

b) digitizing said electric signal;

c) using said digitized electric signal as an input signal to a microprocessor;

d) bringing said digitized electric signal in correspondence with a sequence of musical sound configurations by means of said microprocessor so as each pulse beat is followed by one of said sound configuration in real time;

f) presenting said sequence of musical sound configurations to the patient so as each sound configuration is played in real-time synchrony with respective pulse beat and no longer than until the next pulse beat of the patient.

In a preferred embodiment of the present invention, each of said sound configurations can be a member of a plurality of sound configurations responding to the patient's pulse in a pre-determined order.

The operator, by means of a clock generator, can change the duration of the sound configurations, i.e., the duration thereof whereas general tempo of the music is defined by the patient's pulse.

The aforesaid method does not allow any overlap between the sound configurations. According to the method, a current sound configuration is stopped before the starting of the next sound configuration if the duration of the first of the two configurations is longer than the time interval between the two respective consecutive pulse beats.

Some of aforesaid sound configurations can be played immediately after respective pulse beats, others—with a fixed delay, depending on a program of said microprocessor.

In a preferred embodiment of the invention the musical sound configurations are at first prepared as wave files in a PC by means of a standard mixer-synthesizer program and downloaded into the memory of said microprocessor from said PC by using a communication card and a special program.

The duration of the aforementioned delay, as well as the number and order of said sound configurations can be modified according to individual needs of the patient. This modification is carried out from the PC through the communication interface not in real time.

In a preferred embodiment of the invention, musical arrangement of each of said sound configurations can be altered by means of a performing processor connected to said microprocessor. The alteration is introduced by an operator upon the patient's request and/or according to results of the treatment through a special set-up table.

Aforesaid alteration can also be transmitted from said set-up table to the microprocessor through the Internet.

Furthermore, said musical sound configurations can be modified not in real time according to a digitized sample of the patient's pulse by a program of said PC. Said sample is taken as aforementioned after a certain time period from the beginning of the treatment, depending on the result thereof.

Said digitized sample of the pulse can be transmitted to said PC in real time from the output of the analog to digital converter through the microprocessor.

The method according to the invention also allows the microprocessor to be completely substituted by said PC so that all aforesaid functions of the microprocessor are transferred to the PC.

If said microprocessor and said PC function alongside each other, the method provides for a possibility to download said sound configurations from the PC into the memory of the microprocessor through the Internet.

The digital sample of the pulse can also be transmitted from the microprocessor to the PC through the Internet.

In a preferred embodiment of the invention, the PC can be connected to the Internet in order to modify and substitute said musical sound configurations.

Evaluation of said musical pattern sequence regarding the psychotherapeutic effect thereof is done in advance by an experienced operator guided by their knowledge and intuition on the subject.

According to the method, said sensor can be placed on an artery pulse point or on a fingertip.

The patient's pulse picture can be seen on a computer screen or other display.

The present invention further relates to a device for the realization of the method. According to the method, the device allows presentation to the patient of a sequence of musical patterns in real time synchrony with the patient's heartbeat with relation to every single pulse. The device comprises the following units:

a) a pulse sensor for picking-up the pulse of the patient and converting said pulse into electrical signal;

b) an analog to digital converter operatively connected to said sensor for digitizing said electric signal; (the analog to digital converter is also termed a "digital level translator", and these terms may hereby be used interchangeably);

c) a microprocessor operatively connected to said analog to digital converter for transforming in real time the patient's pulse into a pre-determined sequence of sound configurations, each of said configurations responding to one pulse beat of the patient and lasting no longer than until the next pulse beat.

d) a clock generator for modifying the frequency of said musical sound configurations;

e) headphones or loudspeaker operatively connected to said performing processor for presenting the music to the patient.

To prevent the overlap between the musical patterns, said microprocessor comprises a processing means for stopping said sound configuration before the next sound configuration starts if the duration of the first of the said sound configurations is longer than the time interval between the two respective consecutive pulse beats.

Said microprocessor comprises a processing means providing a certain order of responding by said sound configurations to the patient's pulse beats. That makes the music flexible, melodious and more effective.

The device according to the invention comprises a communication card through which said sound configurations are registered in the memory of said microprocessor from the PC.

The number, order of said sound configurations, as well as the time of delay of a certain sound configuration can be changed from a PC by a special program through another communication card. The microprocessor can be connected with the PC through the Internet.

The two communication cards comprise the communication interface of the device according to the invention.

In a preferred embodiment of the invention, said PC can be connected through the Internet with another PC in order to modify the sound sequences and/or substitute them according to results of the treatment.

In a preferred embodiment of the invention, said digital level translator is connected to the PC through the microprocessor for directly transmitting the patient's pulse to said PC. The connection to the PC can be carried out through the Internet as well.

The device according to the present invention can also comprise a performing midi-processor and a set-up table, both of which are connected to said microprocessor. Said midi-processor is provided with a processing means for altering musical arrangement of each of said sound configurations. This alteration is introduced by an operator through said set-up table that can also be connected to said microprocessor through the Internet. Similar to the aforementioned, in such an embodiment of the invention, the sound configuration are played in real time synchrony with the patient's pulse, a digital electric signal of which enters the microprocessor.

According to the method of the invention, a pressure sensitive or a photoelectric pickup can be used as a pulse sensor.

DETAILED DESCRIPTION OF A PREFERRED EMBODIMENT

The present invention will be described in detail in FIG. 1. This description is not intended to limit the scope of the present invention, but only to illustrate the preferred embodiment.

According to the embodiment, the patient's pulse is picked up by either piezoelectric pressure sensitive or photoelectric sensor 1 and turned into an electric signal. The sensor is fixed in a plastic bucket, which enables to put said sensor on the fingertip.

The signal is transmitted to input filter 2, comprising two filters: a low-pass filter against 50/60 Hz noises with peak-to-peak amplitude of up to 10 V and a high-pass filter which cuts noises from 2000 Hz. From input filter 2 the signal is transmitted to input amplifier 3, which is a differential amplifier with a gain range of 50. Therefrom, the signal goes to output high-pass filter 4, which cuts below 100 kHz.

After filter 4, the signal is digitized by digital level translator 5. Translator 5 transforms said AC signal to a digital level between O, 3 V to 3 V by means of an open collector comparator with a threshold of 0.3 V and hysteresis of 50 mV. The comparator output can reach 5 V.

From converter 5, the signal goes to microprocessor, comprising microcontroller 6, two digital musical processors 6a, clock generator 6c, analog adder 6b and communication interface 6d.

Microcontroller 6 has three units:
1) 8032 microcontroller for general control of sound and communication;
2) The memory:
   16 KBYTES of RAM;
   32 KBYTES of EPROM;
   32 Kbytes of EEPROM;
3) 8254 programmable general-purpose timer, which consists of 3 16-bit-general-purpose timers.

Microcontroller 6 transmits to digital musical processors 6a the sound configurations coming up in real-time synchrony with the patient's pulse beats.

Digital musical processor 6a consists of the single musical record/playback chip, in which the musical sound configurations are recorded.

The 2 digital musical processor outputs are connected to analog adder 6c to give a 2-sounds' mix.

Programmable Clock Generator 6c

The Programmable Clock Generator output is connected (by a jumper) to an input of microcontroller 6 and to the clock inputs of the two digital musical processors and changes the input clock frequency. This change of the input clock frequency of processor 6a changes the tempo of each of said sound configurations whereas general tempo of the music is defined by the patient's pulse. The musical sound configurations are played according to a special program of microcontroller 6.

Output Audio Amplifier 6e

The Output Audio amplifier interfaces between the digital musical processor and the loudspeaker of the headphones. A potentiometer controls the sound volume.

RS232 Communication Interface 6d

The RS232 communication interfaces between an IBM PC and microprocessor 6 for software downloading and debugging.

The invention claimed is:
1. A method for presenting music to a patient, comprising:
(a) sensing the patient's pulse as an analog electric signal;
(b) digitizing said analog electric signal;
(c) using said digitized electric signal as an input signal to a microprocessor;
(d) bringing said digitized electric signal into correspondence with a sequence of musical sound configurations by means of said microprocessor so that each pulse beat is followed by one of said sound configurations in real time; and
(e) in response to a pulse beat, presenting said sequence of musical sound configurations to the patient with a fixed delay that is sufficiently short to avoid overlap between the musical sound configurations and a subsequent pulse beat of the patient so that each sound configuration is played in real-time synchrony with a respective pulse beat.

2. A method according to claim 1 wherein each of said sound configurations is a member of a plurality of sound configurations responding to the patient's pulse beats in a pre-determined order.

3. A method according to claim 1 wherein a current sound configuration is stopped before the successive sound configuration starts if the duration of the current configuration is longer than a time interval between the two respective consecutive pulse beats.

4. A method according to claim 1 wherein said sound configuration is played in response to a pulse beat immediately after said pulse beat.

5. A method according to claim 1 wherein the sound configurations are at first prepared in a computer and downloaded into the memory of said microprocessor through a communication interface.

6. A method according to claim 1, further comprising changing a length of said delay, and a number and order of the sound configurations not in real time.

7. A method according to claim 1 including:
introducing a desired change to a musical arrangement of each of said sound configurations through a set-up table connected to said microprocessor; and
altering the musical arrangement of each of said sound configurations by a midi-processor connected to said microprocessor in response to said desired change.

8. A method according to claim 7 wherein set-up data in said set-up table is transmitted to said microprocessor through the Internet.

9. A method according to claim 1 wherein said digitized electric signal is transmitted from the microprocessor to a computer in real time.

10. A method according to claim 9 wherein said digital electric signal is transmitted from said microprocessor to a computer through the Internet.

11. A method according to claim 1 wherein all functions of said microprocessor are performed by a suitably programmed computer.

12. A method according to claim 1 wherein said sound configurations are transmitted from a computer to a memory of said microprocessor through the Internet.

13. A method according to claim 1 further including evaluation of said music regarding a psychotherapeutic effect thereof.

14. A method according to claim 1 wherein the pulse sensor is placed on an artery pulse point.

15. A method according to claim 1 wherein the pulse sensor is placed on a fingertip.

16. A method according to claim 1 wherein a pulse picture of the patient is presented on a display.

17. A method according to claim 1 wherein said display is a computer screen.

18. A device for presenting music to a patient, said device comprising;
a pulse sensor for sensing the pulse of the patient and converting said pulse into electrical signal;

an analog to digital converter operatively connected to said sensor for digitizing said electric signal;

a microprocessor operatively connected to said analog to digital converter for bringing said digitized electric signal in correspondence with a sequence of musical sound configurations in real time so as to form a modified sequence of musical sound configurations whose tempo is synchronized to the pulse beat;

a midi-processor and a set-up table both connected to said microprocessor, said midi-processor being adapted for carrying out a desired change to a musical arrangement of each of said sound configurations, said change being introduced through said set-up table; and headphones or loudspeaker operatively connected to said microprocessor for presenting the modified sequence of musical sound configurations to the patient.

19. A program storage device readable by machine, tangibly embodying a program of instructions executable by the machine to perform a method for presenting music to a patient, said method comprising:
(a) bringing a digitized electric signal electric signal representative of the patient's pulse into correspondence with a sequence of musical sound configurations so that each pulse beat is followed by one of said sound configurations in real time; and
(b) in response to a pulse beat, presenting said sequence of musical sound configurations to the patient with a fixed delay that is sufficiently short to avoid overlap between the musical sound configurations and a subsequent pulse beat of the patient so that each sound configuration is played in real-time synchrony with a respective pulse beat.

20. A device for presenting music to a patient, said device comprising:
(a) a pulse sensor for sensing the pulse of the patient as an analog electrical signal;
(b) an analog to digital converter operatively connected to said sensor for digitizing said electric signal;
(c) a microprocessor operatively connected to said analog to digital converter and programmed for bringing said digitized electric signal in correspondence with a sequence of musical sound configurations so that each pulse beat is followed by one of said sound configurations in real time with a fixed delay between the pulse beat and a respective sound configuration that is sufficiently short to avoid overlap between the musical sound configurations and a subsequent pulse beat of the patient; and
(d) headphones or loudspeaker operatively connected to said microprocessor for presenting the modified sequence of musical sound configurations to the patient.

21. A device according to claim 20 wherein said microprocessor is programmed to stop a current sound configuration before starting a successive sound configuration if the duration of the current sound configuration is longer than the time interval between the two respective consecutive pulse beats.

22. A device according to claim 20 wherein said microprocessor is programmed to provide a plurality of sound configurations responding to the pulse of the patient in a predetermined order.

23. A device according to claim 20, having a communication interface through which said sound configurations are downloaded into the memory of said microprocessor from a PC coupled to said communication interface.

24. A device according to claim 20, having a communication interface through which the number, order and temporal arrangement of said sound configurations can be changed via a PC coupled to said communication interface.

25. A device according to claim 20 wherein said microprocessor comprises a communication interface for coupling to a PC for recording said sound configurations in a memory chip of said microprocessor and for changing the number, order and temporal arrangement of said sound configurations.

26. A device according to claim 20, further comprising a midi-processor and a set-up table both of which are connected to said microprocessor, said midi-processor being adapted for carrying out a desired change to a musical arrangement of each of said sound configurations, said change being introduced through said set-up table.

27. A device according to claim 20 wherein said microprocessor is completely contained within a computer.

28. A device according to claim 20 wherein said microprocessor is connectable to the Internet for modifying said sound configurations and changing musical arrangement thereof.

29. A device according to claim 20 wherein the analog to digital converter is directly connected to a computer for sending to the computer a digitized sample of the patient's pulse.

30. A device according to claim 29 wherein said analog to digital converter is connectable to the Internet for sending said digitized sample of the patient pulse to a remote computer for analysis and appropriate modifying of said sound configurations.

31. A device according to claim 20 wherein said pulse sensor is a pressure sensitive sensor.

32. A device according to claim 20 wherein said pulse sensor is a photoelectric sensor.

33. A computer program product comprising a computer useable medium having computer readable program code embodied therein for presenting music to a patient, the computer program product comprising:
computer readable program code for causing the computer to bring a digitized electric signal electric signal representative of the patient's pulse into correspondence with a sequence of musical sound configurations so that each pulse beat is followed by one of said sound configurations in real time; and
computer readable program code responsive to a pulse beat for causing the computer to present said sequence of musical sound configurations to the patient with a fixed delay that is sufficiently short to avoid overlap between the musical sound configurations and a subsequent pulse beat of the patient so that each sound configuration is played in real-time synchrony with a respective pulse beat.

* * * * *